United States Patent
Kaza et al.

(10) Patent No.: US 10,709,120 B2
(45) Date of Patent: Jul. 14, 2020

(54) PEROMYSCUS ANIMAL MODEL FOR CANCER

(71) Applicant: University of South Carolina, Columbia, SC (US)

(72) Inventors: Vimala Kaza, Lexington, SC (US); Eleni Farmaki, Columbia, SC (US); Ioulia Chatzistamou, Irmo, SC (US); Hippokratis Kiaris, Irmo, SC (US)

(73) Assignee: University of South Carolina, Columbia, SC (US)

( * ) Notice: Subject to any disclaimer, the term of this patent is extended or adjusted under 35 U.S.C. 154(b) by 30 days.

(21) Appl. No.: 15/877,510

(22) Filed: Jan. 23, 2018

(65) Prior Publication Data

US 2018/0206466 A1    Jul. 26, 2018

Related U.S. Application Data

(60) Provisional application No. 62/449,303, filed on Jan. 23, 2017.

(51) Int. Cl.
*A01K 67/033* (2006.01)
*A01K 67/02* (2006.01)

(52) U.S. Cl.
CPC ............ *A01K 67/033* (2013.01); *A01K 67/02* (2013.01); *A01K 2217/15* (2013.01); *A01K 2227/105* (2013.01); *A01K 2267/03* (2013.01)

(58) Field of Classification Search
None
See application file for complete search history.

(56) References Cited

PUBLICATIONS

Steger et al (abstract) (Year: 1980).*
Navara et al (J. Pineal Res, 43:215-224, 2007 (Year: 2007).*
Nelson et al, (Journal of Biological Rhythms, 9(3-4): 233-249, 1994 (Year: 1994).*
Hill et al (Journal of Mammary Gland Biology and Neoplasia. 16 (3): 235-45, 2011). (Year: 2011).*
U.S. Appl. No. 62/449,303, filed Jan. 23, 2017.
Bedford NL, Hoekstra HE. "Peromyscus mice as a model for studying natural variation." Elife. Jun. 17, 2015;4. doi: 10.7554/eLife.06813.
Bennett, et al. "Evaluation of cyclosporine-treated mice as hosts for growing and testing the chemosensitivity of first-transplant-generation human tumor xenografts implanted under the kidney capsule." *J Natl Cancer Inst*. Nov. 1985;75(5):925-36 (Abstract Only).
Churchill, et al., "Complex Trait Consortium." The Collaborative Cross, a community resource for the genetic analysis of complex traits. Nat. Genet. 2004; 36: 1133-1137.
Day, et al. "Preclinical mouse cancer models: a maze of opportunities and challenges." *Cell*. Sep. 24, 2015;163(1):39-53.
Farmaki, et al. "A Ccl8 gradient drives breast cancer cell dissemination. Oncogene." In Press, 2016.
Fingert, et al.. "Transplantation of human or rodent tumors into cyclosporine-treated mice: a feasible model for studies of tumor biology and chemotherpay." *Proc Natl Acad Sci* U S A. Dec. 1984;81(24):7927-31.
Goodman, et al. "A model of human melanoma in cyclosporine-immunosuppressed rats." J Invest Dermatol. Feb. 1987;88(2):141-4.
Havighorst, et al., "Modeling Disease in Peromyscus." Seminars in Cell and Developmental Biology. In Press. 2016 (Abstract Only).
Svenson, et al., "High-resolution genetic mapping using the Mouse Diversity outbred population." G.A. Genetics. 2012; 190: 437-447.
Wade CM, Daly MJ. Genetic variation in laboratory mice. Nat Genet. Nov. 2005; 37(11):1175-80.

* cited by examiner

*Primary Examiner* — Anoop K Singh
*Assistant Examiner* — Magdalene K Sgagias
(74) *Attorney, Agent, or Firm* — Dority & Manning, P.A.

(57) ABSTRACT

A nonhuman animal cancer model is described. The animal model includes an animal of the genus *Peromyscus* and xenograft cancer cells implanted in the animal. Methods for utilizing the animal model can include evaluation of growth and development of cancer cells as well as evaluation of known and potential cancer treatment therapies. The animal model can be utilized to examine the efficacy of an anticancer therapy at the preclinical stage, can be utilized to screen potential cancer treatments in an individualized cancer treatment protocol, and can be utilized for identification of biomarkers associated with particular cancers and/or particular anticancer therapies, among other beneficial uses.

4 Claims, 4 Drawing Sheets

PEROMYSCUS ANIMAL MODEL FOR CANCER

CROSS REFERENCE TO RELATED APPLICATION

This application claims filing benefit of U.S. Provisional Patent Application Ser. No. 62/449,303 having a filing date of Jan. 23, 2017, which is incorporated herein by reference for all purposes.

BACKGROUND

The prime effort in research on cancer management is directed toward the development and improvement of innovative therapeutics. Unfortunately, while many experimental anticancer therapies show promising results in preclinical studies, they fail to reproduce the results in the clinical setting. For instance less than 5% of treatments that enter clinical trials go on to be approved for use in humans and over 70% of all drug development costs are attributed to costs associated with failed drugs. One of the key components in this high failure rate is that the vast majority of preclinical studies are performed using animal models based on laboratory mice that are associated with several limitations that account at least in part for the reduced predictive value for human cancer and modest efficacy of current therapies.

A major limitation of laboratory mice-based animal models in cancer-related studies is related to their inbred nature. By not representing wild type (outbred) genomes they hardly reflect either human or even wild type mouse populations. Thus, they can model only a fraction of the natural human population and to that end the discrepancies between the results of preclinical studies in mice and those of studies in patients are not surprising. This issue can be particularly relevant to the pharmacological studies in which the activity of a given drug can be tightly related to the genetic makeup of the host.

Efforts to overcome this limitation have been undertaken, such as through the establishment of the "collaborative cross" in *Mus* that through a series of designed successive breeding aimed to develop a genetically heterogeneous mouse population with defined characteristics. Although informative to some extent, intrinsic limitations restrict its value due primarily to the fact that along with 3 wild-derived strains, 5 inbred strains participate in the maintenance of this population.

Such issues concerning the low predictive value of animal models for anticancer therapies mandates the development of preclinical models with better predictive value. Development of experimental models that better simulate the human disease and therefore exhibit increased predictive value during preclinical testing would be of considerable value. For instance, use of naturally occurring outbred animal populations that mimic the human cancer process may overcome limitations and may provide experimental models that better represent naturally occurring wild type populations offering genetic variation similar to that seen in human populations and improved preclinical study outcomes.

SUMMARY

According to one embodiment, disclosed is a nonhuman animal model system for cancer research. The nonhuman animal model includes an animal of the genus *Peromyscus* and xenograft cancer cells in which the xenograft cancer cells have been implanted in the animal. For instance, the xenograft cancer cells can be human cancer cells implanted in an animal of the *Peromyscus* genus.

Also disclosed is a method for producing the animal model and methods for utilizing the animal model. Methods for using the animal model can include evaluation of growth and development of cancer cells as well as evaluation of potential cancer treatment therapies. For instance the animal model can be utilized to examine the efficacy of an anticancer therapy at the preclinical stage. In one embodiment, the animal model can be utilized to screen potential cancer treatments in an individualized cancer treatment protocol. The animal model can also be utilized for identification of biomarkers associated with particular cancers and/or particular anticancer therapies.

In one embodiment, a method for using the animal model can include initiating a potential anticancer therapy to an animal of the genus *Peromyscus*, the animal carrying implanted xenograft cancer cells. The method can also include studying the effects of the therapy on the cancer cells and/or on the animal. For instance, the method can include comparing one or more physical characteristics of the animal to those of another animal of the same species that does not carry the implanted human cancer cells. In one embodiment a method can include comparing physical characteristics of an animal treated with an anticancer therapy with those of another animal of the same species that also carries the implanted xenograft cancer cells but receives a different or no anticancer therapy.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which.

Repeat use of reference characters in the present specification and drawings is intended to represent the same or analogous features or elements of the present invention.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

In general, the present disclosure is directed to animal models for use in studying cancer, and in one embodiment for studying anticancer treatments. More specifically, an animal model can utilize an animal of the genus *Peromyscus* (deer mice) in conjunction with implanted xenograft cancer cells. This particular genus can be attractive for use in an animal model as populations of this genus can be maintained in captivity and can accurately mimic the cancer disease process and therapy response of other types of animals and in particular of humans.

In one embodiment, the animal model can utilize an outbred species of the *Peromyscus* genus. As utilized herein, the term "outbred" generally refers to animals within a group of which there is some genetic variation and for whom inbreeding has been minimized to not more than about 1% per generation, for instance as can be achieved with random mating using about 25 or more breeding pairs per generation. For instance, a colony can include about 100 or more breeding pairs, or even more in some embodiments. As such, genetic drift due to inbreeding can be minimal, though the stock characteristics may change as a result of selective breeding or the like.

Another benefit of the animal model is that *Peromyscus* live considerably longer than laboratory mice (5-8 years for the former as compared to 2-3 years for the latter), which is particularly advantageous considering that cancer is a disease that primarily affects the elderly. Utilizing the *Peromyscus* animal model that readily allows the evaluation of the effects of aging in drug efficacy may be especially valuable in some embodiments.

Any species of the *Peromyscus* genus can be utilized as the animal of the model including, without limitation, those of the groups *californicus, eremicus, hooperi, crinitus, maniculatus, leucopus, aztecus, truei, melanophrys, furvus, mealops*, and *mexicanus*. In one embodiment, the animal of the model can be of the *P. californicus* species. *P. californicus* is the physically largest *Peromyscus* species (adult weight is about 42 g) and has a lifespan exceeding 5.5 years in captivity. *P. californicus* has been used for behavioral studies as it has a social organization that is monogamous, with males and females forming long-term relationships. Males help care for the young, and the male's presence increases their chance of survival. In view of the role of sex hormones in regulating such behavioral traits the value of this animal as a cancer model increases by the fact that it exhibits patterns similar to those of humans, and divergent from those of laboratory mice.

Preferred species for use in a study can vary depending upon factors such as, and without limitation to, the particular cancer to be studied, the presence and type of immunosuppression to be used in the study, the type and delivery mode of the anticancer therapy, etc. For instance, when utilizing the animal model with breast cancer cells, it may be beneficial to utilize a species with increased mitogenic properties (e.g., relatively shorter lifespan), and/or larger average size such as *P. californicus*. However, it should be understood that the animal model is not limited to any particular species of the genus. The particular species can also be chosen based upon natural levels of materials in the animals.

For instance, a species in which the natural level of one or more hormones involved in the particular cancer being studied is similar to that of humans can be a good candidate for an animal model studying that particular cancer. By way of example, *P. californicus* can have a plasma estradiol level of between about 10 pg/mL and about 45 pg/mL, which is much higher than the typical mouse plasma estradiol level (about 3 pg/mL to about 5 pg/mL) and much closer to the typical level of post-menopausal women (about 50 pg/mL). As such, the *P. californicus* species can be a good candidate when studying ER positive breast cancers.

The animal model can be utilized in studying cancer development and/or anticancer therapies by implantation of the animals with xenograft cancer cells of interest. In particular, the *Peromyscus*-based animal model can be utilized in research directed to any cancer cells or cancerous disease as well as to therapies for use in any aspect of a disease process including, without limitation, early stage, late stage, adjuvant treatments, etc.

The terms "cancer" and "cancerous" as utilized herein refer to or describe the physiological condition in mammals that is typically characterized by unregulated cell growth. Included in this definition are benign and malignant cancers as well as dormant tumors or micrometastases. Examples of cancer include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblasts leukemia; and post-transplant lymphoproliferative disorder (PTLD), as well as abnormal vascular proliferation associated with phakomatoses, edema (such as that associated with brain tumors), and Meigs' syndrome.

The cancer cells to be implanted can be obtained from a known cancer cell line or can be from a particular patient or study group, for instance in examination of a personalized cancer therapy. For example, human cancer cells may be obtained directly from a human tumor (e.g., biopsy material), for example, or from a primary culture. The human cancer cells can then be directly implanted in the animal or can be implanted following a period of ex vivo culturing. The implanted cancer cells may originate from a primary tumor or from a metastasized tumor. The implanted cancer cells may be orthotopic (originating from the same anatomic location as the site of implantation) or heterotopic (obtained from an anatomic site other than the implantation site.

In general, the species of the cancer cells implanted to the animal model is human. However, the cancer cells may be obtained from a non-human animal species, in which case the animal model may be used for veterinary study and the patient can be a non-human animal (a veterinary patient) from which the primary cancer cells are obtained. For example, the one or more primary cancer cells can be those of a domesticated farm animal or pet, or other non-human animal.

The cancer cells implanted in or on tissue of the animal in can be in isolated form, or can include other cells and/or materials (as a crude specimen), at the time of implantation. Optionally, the cancer cells may be purified or undergo selection techniques (e.g., using flow cytometry) in order to implant only primary cancer cells or only subsets of primary cancer cells, such as cancer stem cells. In some embodiments, the cells are implanted as a tissue.

Optionally, the cancer cells may be stored prior to implantation using methods known in the art (e.g., frozen) that would not be incompatible with the viability of the cells when implanted. Suitable storage conditions will depend on the cancer type. Typically, cells of high grade, aggressive tumors survive better and longer than low grade tumor cells. If cancer cells are subsequently harvested from the animal model, the harvested cells may also be stored for a time. Harvested cells may be expanded (cultured) and implanted in multiple animals in series or parallel for further assessments, and this process may be repeated any number of times.

The implanted cells may bear a detectable label (e.g., a bioluminescent label such as luciferase). The implanted cells may carry a heterologous nucleic acid. The nucleic acid may encode, for example, a detectable label. Many detectable labels are known in the art and may be utilized. Depending upon the type, the label may be imaged using an imaging instrument. Methods and markers commonly used to identify cells and to distinguish cell types as are described in the scientific literature (e.g., Stem Cells: Scientific Progress and Future Research Directions, Appendix E1-E5, report prepared by the National Institutes of Health, June, 2001) can be implanted in conjunction with the cells.

The number of cancer cells included in the implantation can be determined by those skilled in the art. In some embodiments, approximately 1,000 to about 5,000,000 cancer cells are implanted. Any implantation technique effective in delivering the cells to the animal can be utilized. For example, breast cancer cells can be implanted in or on the breast in an open surgical manner (laparotomy) or through direct injection. In some embodiments, the cancer cells can be implanted in conjunction with a second cell type. For instance, human cancer cells can be implanted in conjunction with (e.g., admixed with) human stromal fibroblasts, as is known with other animal models.

The animals can generally be immunosuppressed during a study by use of an administered immunosuppression agent. One way of inducing acceptance of xenograft cancer cells is the administration of Cyclosporine A (CsA), a cyclic fungal peptide produced by *Tolypocladium inflatum* Gams. CsA is a neutral cycloundecapeptide with potent immunosuppressive properties (Borel, 1989; Di Padova, 1989; Hess et al, 1988). This antifungal metabolite appears to inhibit both humoral and cellular immune responses by selectively interfering with T-cell activation (Borel, 1989; Di Padova, 1989; Hess et al, 1988). CsA has been shown to be effective in preventing transplant rejection in both humans and animals In one embodiment, ketoconazole can be utilized in conjunction with CsA as a means of reducing the dose of CsA required to maintain immunosuppression and prevent graft rejection (Gandhi et al, 1992; Butman et al, 1991; First et al, 1991; Wadhwa et al, 1987). Ketoconazole is a synthetic imidazole dioxolane used primarily for the treatment of superficial fungal infections, chronic mucocutaneous candidiasis and genital candidiasis (Bodey, 1992; Breckenridge, 1992; Borelli et al, 1979). Ketoconazole indirectly enhances the bioavailability of CsA by inhibiting the hepatic cytochrome P-450 mixed function oxidase system which is primarily responsible for CsA inactivation in vivo (Breckenridge, 1992; First et al, 1991; Wadhwa et al, 1987). Increased bioavailability reduces the dose of CsA required for therapeutic efficacy, which, in turn, decreases the toxicity associated with its use.

Conceptually, a limitation of applying CsA-mediated immunosuppression during a testing protocol is that CsA may directly impact tumor growth. Indeed, some earlier studies have recognized antitumor activity in CsA despite its tumor-promoting action through immunosuppression. However, as it is commonly known that it is likely in the context of (cytotoxic) chemotherapy that CsA may interfere with drug efficacy, one of skill in the art will understand that the effects of CsA in the growth of cancer cells in combination with the therapy under investigation can be explored in vitro prior to testing them in CsA-treated animals. Those of skill in the art are fully capable of carrying out such investigation and and interpreting the results accordingly. It is well known that as opposed to genetically-mediated immunosuppression and for which inbreeding is inherent for the production and maintenance of the mutant animals, in order to perform experiments in outbred population as is described herein, pharmacological immunosuppression is likely unavoidable.

In one embodiment, the animal model can be utilized for evaluating typical cancer cell growth. Such a method can include evaluating the growth of the xenograft cancer cells following implantation thereof in the animal. Evaluation of cancer cell growth following implantation can be carried out ex vivo and/or in vivo according to known practice. For example, evaluation of cancer cell growth may be carried out in vivo with an imaging modality selected from among one or more of bioluminescent imaging, (e.g., luciferase), ultrasound imaging, and magnetic resonance imaging (MRI) (e.g., anatomical MRI, diffusion MRI, MRI spectroscopy, dynamic contrast enhanced (DCE) MRI). Depending on the modality utilized, labels and imagining agents may be re-administered to the cancer cells or the animal model periodically (e.g., by injection) as needed (e.g., for longitudinal studies). Optionally, pre-administration and pre-implantation images may be taken for comparison to subsequent images taken under the same or different conditions for evaluation of cancer cell growth (e.g., post-treatment).

In one embodiment, a method of studying a particular cancer can be carried out by use of the animal model. For instance, a method can include evaluating at least one parameter of the xenograft cancer cells and/or the animal model following implantation of the cancer cells. In some embodiments, the evaluation includes gene expression profiling the cancer cells after implantation and/or the animal after implantation. In some embodiments, the parameter comprises the presence or absence of a biomarker (e.g., a single nucleotide polymorphism (SNP)). In some embodiments, the biomarker comprises one or more tumor markers. In some embodiments, the biomarker is a gene expression signature and the method further comprises recording the gene expression signature (e.g., an expression level) in a computer readable medium.

In some embodiments, a biologically active agent can be administered to the animal before, during, and/or after implantation of the xenograft cancer cells and the response of the cancer cells to the biologically active agent can be evaluated ex vivo and/or in vivo. A biologically active agent can be a known or potential cancer therapy agent, but it should be understood that the invention is not limited to such agents. For instance, in one embodiment, a biologically active agent can include an environmental agent that may positively or negatively affect the implanted cancer cells.

The animal model may be utilized to evaluate the effect of one or more known or potential (e.g., preclinical) anticancer therapies on the xenograft cancer cells and/or on the animal. Anticancer therapies as may be studied by use of the animal model can include any type of anticancer therapy or combination thereof including, without limitation, chemical-based therapies (e.g., in preclinical drug testing), radiation-based therapies, surgical-based therapies, immunosuppression-based therapies, alternative therapies, etc. For instance, in one embodiment, the animal model can be utilized in studying adjuvant therapy, which refers to treatment administered following removal of all detectable disease, typically by surgery. The aim of adjuvant therapy is to target residual disease and improve disease free and overall survival. For instance, following implantation of xenograft cancer cells in the animal, a cancerous tumor can be allowed to develop. The adjuvant therapy to be examined can be administered following surgical removal of the tumor, optionally following or in conjunction with other traditional anticancer therapies such as traditional chemotherapies and/or radiation therapies. "Tumor", as used herein, refers to all neoplastic cell growth and proliferation, whether malignant or benign, and all pre-cancerous and cancerous cells and tissues.

A treatment can be administered at a time that the animal carries the cancer cells and exhibits disease symptoms and/or can be administered prior to implantation, e.g., as a prophylactic, or after removal, e.g., as an adjuvant treatment. Thus, a treatment can be administered to the animal before, during, and/or after implantation of the xenograft cancer cells and the response of the cancer cells and/or the animal to the treatment can be evaluated ex vivo and/or in vivo. Optionally, a combination of therapies can be administered and the effect is evaluated. For instance, a combination of one or more chemical treatments and/or physical treatments (e.g., radiation) can be evaluated. In some embodiments, the biologically active agent is a chemotherapeutic agent or other anti-cancer agent. However, the biologically active agent may be a non-anti-cancer agent. Optionally, the method of evaluating cancer cell growth further comprises recording the sensitivity/resistance of the cancer cells to the anti-cancer agent in a computer readable medium.

As used herein, the terms "administering" or "administer" are defined as the introduction of a substance (such as biologically active agents) into cells in vitro, ex vivo, or into the body of a subject in vivo by any route (for example, oral, nasal, ocular, rectal, vaginal and parenteral routes). Substances may be administered individually or in combination with other agents via any route of administration, including but not limited to subcutaneous, intramuscular, intravenous, intraperitoneal, intradermal, via the nasal, ocular or oral mucosa, or orally. For example, substances can be administered by direct injection into or on a tumor, or systemically (e.g., into the circulatory system).

As utilized herein, "implantation" refers to the administration of cells (e.g., one or more primary cancer cells) in vivo. Any implantation technique effective in delivering the cells to the target anatomical site can be utilized. For example, the cells can be implanted in or on an organ in an open surgical manner or through a catheter.

As used herein, the terms "treat" or "treatment" refer to both therapeutic treatment and prophylactic or preventative measures, wherein the object is to prevent or slow down (lessen) an undesired physiological change or disorder, such as the development or spread of cancer, reduce the growth of cancer cells, reduce tumor size, inhibit tumor growth, etc. For purposes of this disclosure, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. For example, treatment may include reduction of undesirable cell proliferation, and/or induction of apoptosis and cytotoxicity. "Treatment" can also mean prolonging survival as compared to expected survival if not receiving treatment. Those in need of treatment include those already with the condition or disorder as well as those prone to have the condition or disorder or those in which the condition or disorder is to be prevented or onset delayed. Optionally, the subject may be identified (e.g., diagnosed) as one suffering from the disease or condition (e.g., cancer) prior to administration of the treatment. Examples of treatment include but are not limited to, chemotherapy, radiation therapy, immunotherapy, or a combination of two or more of the foregoing. A "candidate treatment" may be a treatment that has been previously identified to have efficacy in treating at least some cancer types in vitro or in vivo, or the candidate treatment may have no known efficacy in treating cancer.

The animal model can also be utilized for screening potential treatments for a cancer in a subject. For instance, a method of using the animal model can include implanting cancer cells from the subject in the *Peromyscus* animal and administering a candidate treatment to the animal before, during, or after said implanting. At least one parameter of the cancer cells and/or the animal that is associated with the cancer treatment efficacy or lack of efficacy can then be evaluated. The candidate treatment may be, for example, a chemotherapeutic treatment or other anti-cancer treatment, such as an immunologic treatment, a radiation treatment, or any combination of two or more anti-cancer treatments. The parameter(s) evaluated may be parameters of the cancer cells and/or the animal that provide information as to whether the candidate treatment is effective in treating the cancer. For example, the at least one parameter may comprise cancer cell growth rate or tumor size. In some embodiments, the evaluation can include imaging at least a portion of the animal to determine the response of the one or more human cancer cells to the candidate treatment.

In some embodiments, implanting comprises implanting xenograft cancer cells from the subject in a plurality of animals, and the administration step comprises administering a candidate treatment to each animal before, during, or after implanting the one or more cancer cells. In some embodiments, a different candidate treatment is administered to each animal. In some embodiments, in order to obtain information concerning effective dose or optimum dose, a different dose of the same candidate treatment can be administered to each animal. In some embodiments of the screening method, the method further comprises selecting and administering the candidate treatment to the subject if the results of the evaluation are consistent with cancer treatment efficacy.

By way of example, in one embodiment, the highly sensitive and cost effective short term functional pharmacodynamic assay (MATEX) can be utilized in an evaluation. The MATEX assay can simultaneously analyze multiple signaling pathways in small human tumor tissue explants and fine needle aspiration biopsy samples in a quantitative manner with each tumor becoming its own control. This approach allows the screening of a large number of drugs to predict in vivo efficacy before systemic treatment. This approach can be used with the animal models and methods to allow enrichment of "xenograft trials" for instance by pre-selecting the most effective drugs for each patient tumor line to obtain meaningful data in a most cost effective way and by using the smallest number of animals, which can significantly decrease the cost of drug treatment studies. Previous and ongoing clinical studies have shown that tumor cells obtained by endoscopic/core or fine needle aspiration biopsies prior to initiation of therapy can be successfully assayed ex vivo to predict the in vivo pharmacodynamic effects of targeted drugs in cancer patients (Altiok et al., Int J. Oncol. 2010, 36:19-27). Thus, in some embodiments, a method can include obtaining a sample of cancer cells from a subject and assessing the therapeutic potential of a treatment (such as an anti-cancer agent) ex vivo, as a pre-screen, before screening potential treatments in the animal model. Methods for assessing therapeutic potential are known to those of skill in the art. For example, a method can include obtaining a sample of cancer cells from a subject, treating the sample with one or more candidate treatments ex vivo, and determining whether the response of the cancer cells in the sample is consistent with clinical efficacy in vivo. Those treatments identified to have therapeutic potential can then be used in the screening method with the animal model.

While disclosed methods can be beneficially utilized to examine one or more therapies previously determined to have efficacy in the treatment of at least some cancers in at least some patients or patient populations. The animal model may be aimed at drug discovery, in which the candidate treatment has not previously been identified to have efficacy in the treatment of cancer in vivo. Thus, if the objective is drug discovery, as opposed to the identification of an effective treatment for any single cancer, the method can be a method for screening potential cancer treatments, comprising implanting xenograft cancer cells in an animal of the genus *Peromyscus* and administering one or more candidate treatments to the animals before, during, or after said implanting. A method can also include evaluating at least one parameter of the xenograft cancer cells and/or the animal that is associated with cancer treatment efficacy or lack of efficacy. The screening method can be carried out in parallel with multiple types of cancers and multiple candidate treatments, in high throughput fashion.

In some embodiments, the methods can include harvesting the propagated xenograft cancer cells from the animal after the cells have been allowed to propagate in the animal. Optionally, cancer cells harvested from an animal may be placed in storage. In some embodiments, the method further comprises culturing (expanding) the harvested cancer cells and, optionally, storing the harvested cells. Optionally, harvested cancer cells may be cultured and/or stored and one or more of the cultured and/or stored cancer cells may be implanted in the same or another animal. This process may be carried out repeatedly—in series, in parallel, or both. "Libraries" of animal models and cancer cells (e.g., tumor tissues) grown in animal models can be prepared and characterized based on biomarkers of the subject they were obtained from, based on biomarkers of the cancer cells themselves, and/or based on cancer treatments that the cancer cells are sensitive to or resistant to.

In yet another embodiment, the animal model can be useful in identifying a biomarker for cancer and/or for cancer treatment. For instance, a method can include administering a cancer treatment to a plurality of animals of the *Peromyscus* genus (generally of the same species, but this is not a requirement) that have been previously implanted with xenograft cancer cells and identifying a biomarker that is common to the identified animals. A biomarker can be associated with the particular cancer or optionally can be associated with (correlates with) a treatment to which at least a portion of the animals have been subjected. Thus, in one embodiment, a method can be utilized to identify a biomarker that is associated with a treatment's effectiveness.

The present disclosure may be better understood with reference to the Examples set forth below.

Example 1

Daily cyclosporine (CsA) at 50 mg/kg s.c. was administered in *P. californicus* and *P. leucopus* females about 5 months old, after implantation of 2 million of MDA-MB-231 cells admixed with human HFFF2 fibroblasts (1 million fibroblasts). CsA at this dosage has been previously shown to cause immunosuppression in mice and rats permitting the growth of human cancer xenografts.

Figure 1:
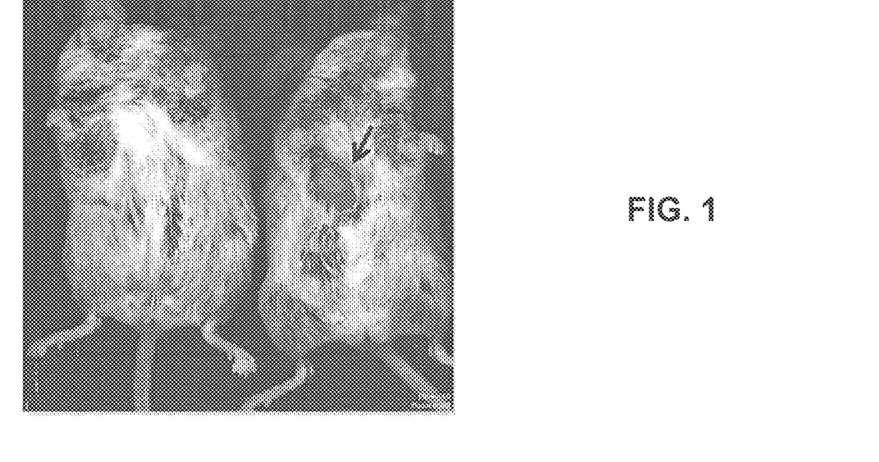
FIG. 1 presents whole body imaging showing a tumor free (left) and a luciferase expressing MDA-MB-231 tumor-bearing (right) *P. californicus*.
Figure 2:
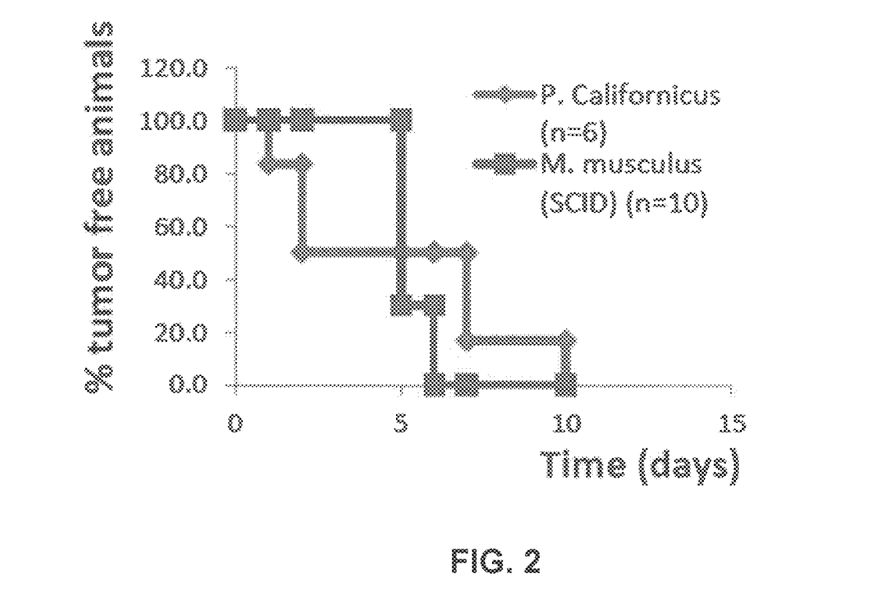
FIG. 2 graphically illustrates tumorigenecity of MDA-MB-231 cells admixed with human HFFF2 fibroblasts and implanted in SCID mice or cyclosporine A (CsA)-treated *P. californicus*.

As control, the same admixture of MDA-MB-231/HFFF2 cells was implanted into immunoincompetent SCID mice. As shown in FIG. 1 and FIG. 2 tumors grew in both SCID mice and *P. californicus* and the animals exhibited similar tumor growth rates.

Figure 3:
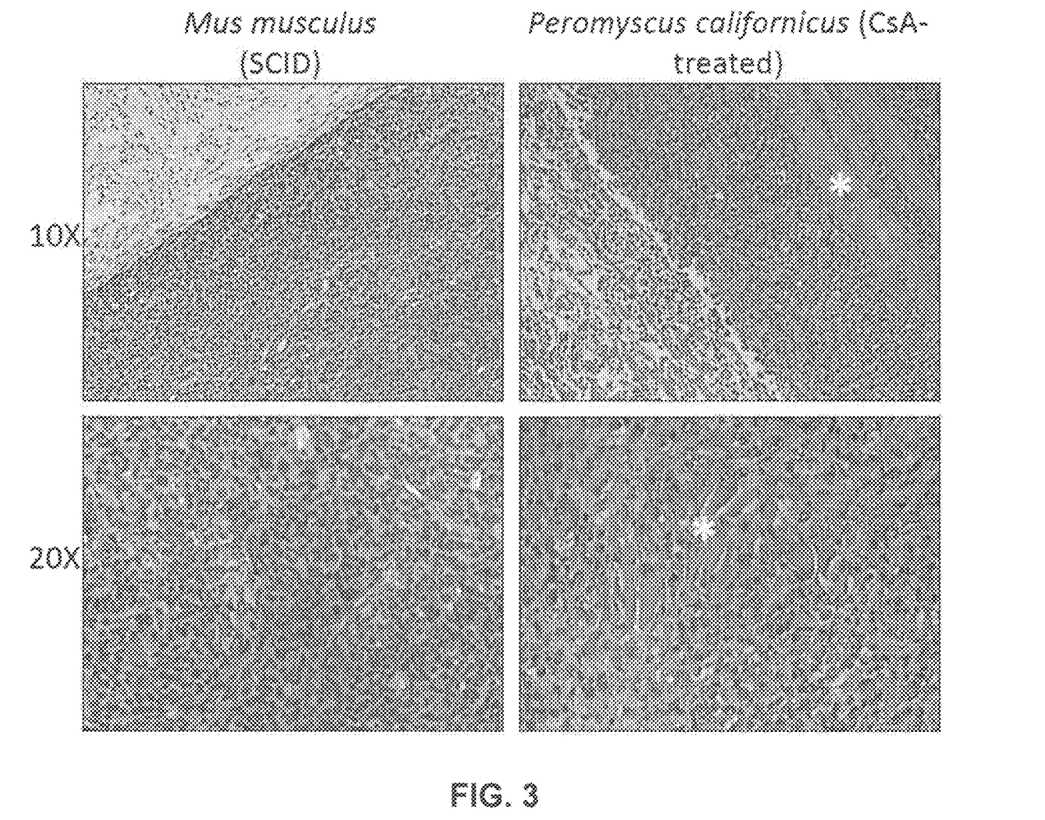
FIG. 3 demonstrates the histology of tumors from MDA-MB-231 admixed with human HFFF2 fibroblasts in SCID (left panel) and *P. californicus* (right panel). Asterisks (*) indicate muscle infiltration.
Figure 4:
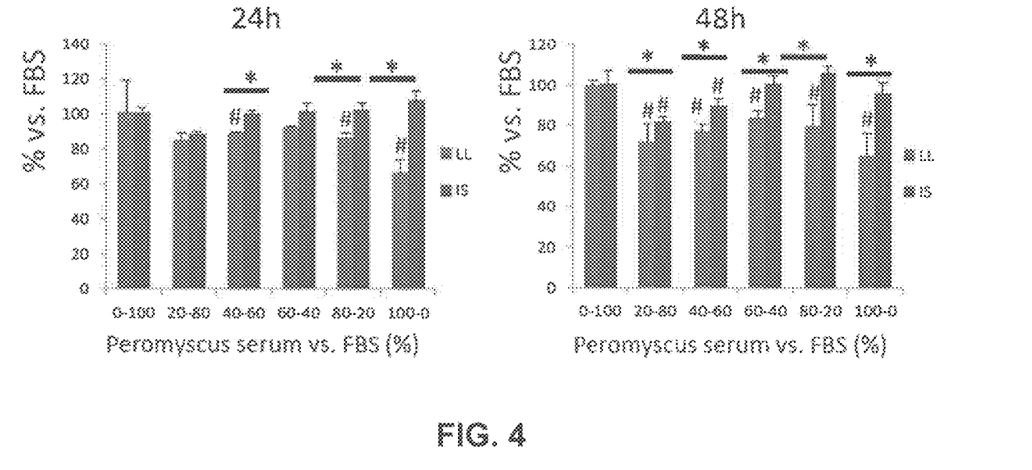
FIG. 4 graphically demonstrates the growth of MDA-MB-231 cells in the presence of different concentrations of *Peromyscus* (LL, *P. leucopus*; IS, *P. californicus*) serum mixed with FBS. *, $P<0.05$; #, $P<0.05$ vs. FBS.

As shown in FIG. 3, histologically, in *P. californicus* muscle infiltration was apparent which is consistent with the aggressive growth of MDA-MB-231 cells in vivo. Interestingly, in *P. leucopus* tumors did not grow, which was believed to be due at least in part to reduced mitogenic potential of *P. leucopus* sera as compared to sera of *P. californicus* (FIG. 4). This observation may be of value in view of the extended lifespan of *P. leucopus* vs. *P. californicus* (8.4 years vs. 5.4 years) and may reflect protective antitumorigenic activity in the former as compared to the latter.

It was also noted that tumor growth in the CsA-treated *Peromyscus* as compared to SCID mice were similar suggesting that CsA did not profoundly affect cancer cell kinetics in vivo. In particular it was demonstrated that CsA-mediated immunosuppression allowed growth of human cancers in *Peromyscus*, especially in *P. californicus*. In view of the unique properties of these animals in terms of outbred nature in captivity and the their extended lifespan as compared to laboratory mice, these animals can provide an improved alternative for studies evaluating anticancer drug efficacy in the context of pre-clinical testing. In addition, the distinct mitogenic properties between different *Peromyscus* species as demonstrated here can form the basis for the discovery of novel mitogenic and/or cytostatic factors between species of the genus.

Example 2

Figure 5:
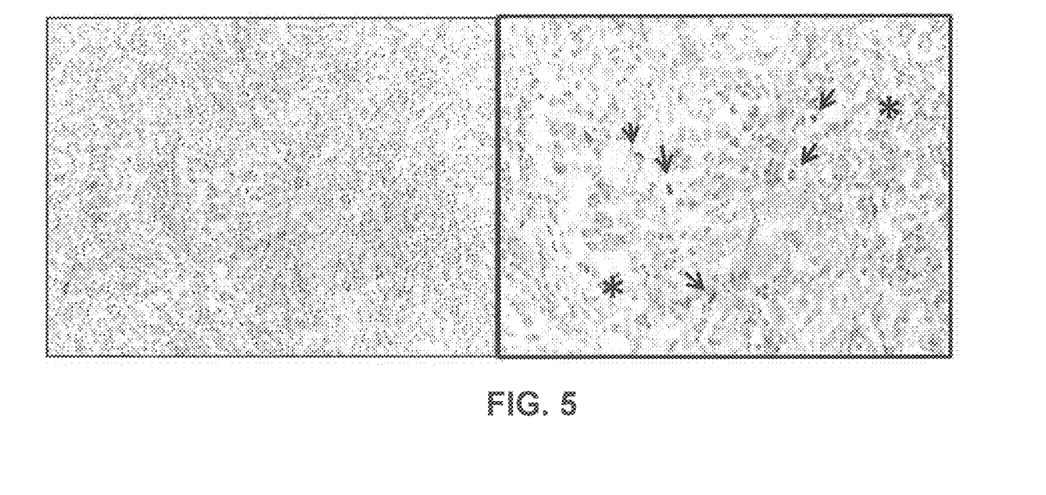
FIG. 5 presents illustrates the histology of MCF7 tumors growing in *P. californicus* with no E2 supplementation at 20× magnification (left) and 40× magnification (right).

*P. californicus* was examined as a host for breast tumor growth using ER(+) human breast cancer cells. The human estrogen-dependent MCF7 breast cancer cells that in mice require E2 supplementation for adequate growth were utilized. 3 million MCF7 cells admixed with 1 million HFFF2 human stromal fibroblasts were implanted in the fat pad of female *P. californicus*. The animals were administered daily CsA. Of the 5 mice implanted with the MCF7 cells, a palpable tumor grew in one animal that after 3 weeks reached a size of about 150 mm$^3$. The tumor was characterized by nuclear pleomorphism, several actively proliferating cells and occasional neutrophil accumulations, resembling the histology of ER-positive breast cancers in women (FIG. 5—mitotic figures are indicated by the arrows and neutrophils' accumulation are indicated by the asterisks in the figure). In the remaining 4 animals only palpable nodules could be detected at which histology indicated the presence of "scar tissue".

It was then hypothesized that different endogenous E2 levels may account for the distinct tumor-promoting activities of the different animals. Thus, plasma E2 levels were assessed and found to range between 13.97 pg/ml-44.79 pg/ml with the animal bearing the tumor having 22.89 pg/ml estradiol in the plasma. This implied that the distinct tumor-promoting activities of the different animals recorded were not directly related to their E2 levels. It was noteworthy that all values exceeded the typical mouse (*Mus*) values that are usually at the range of 3-5 pg/ml and approached the levels of post-menopausal women that range at about 50 pg/ml.

Figure 6:
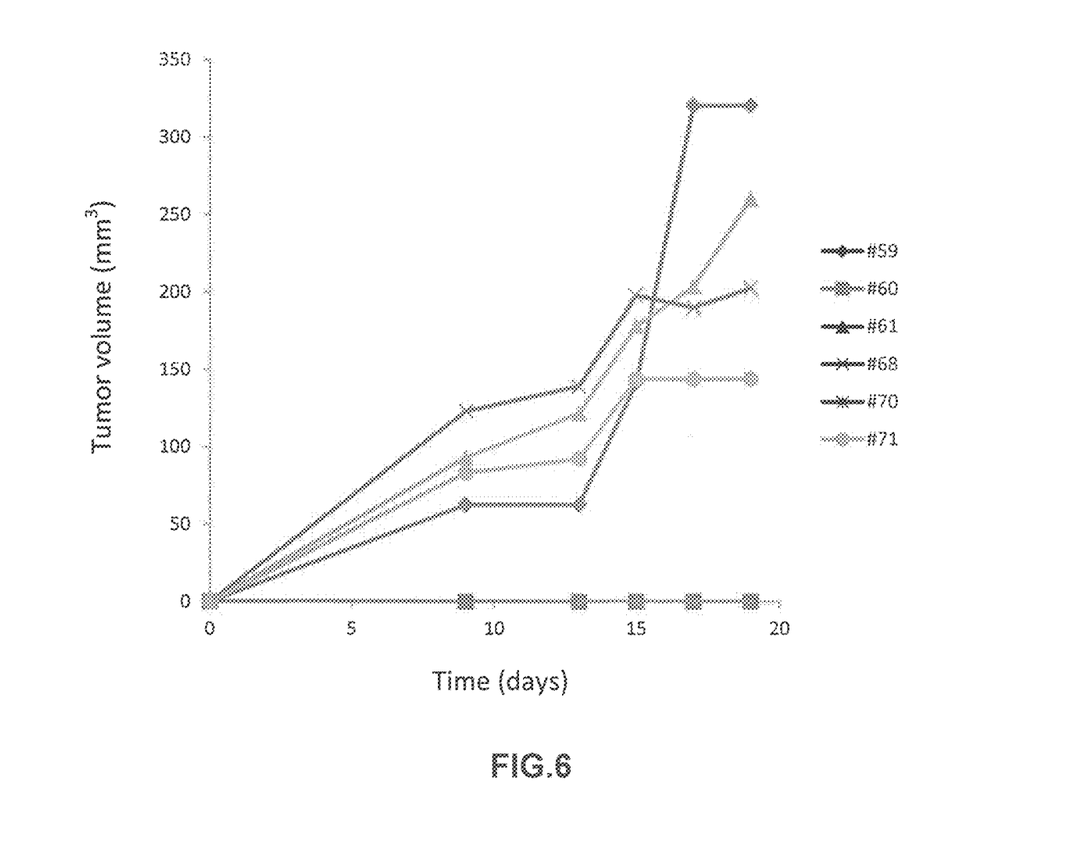
FIG. 6 presents the tumor growth rate of MCF7 ER(+) breast cancer cells admixed with human HFFF2 fibroblasts showing individual tumor volumes
Figure 7:
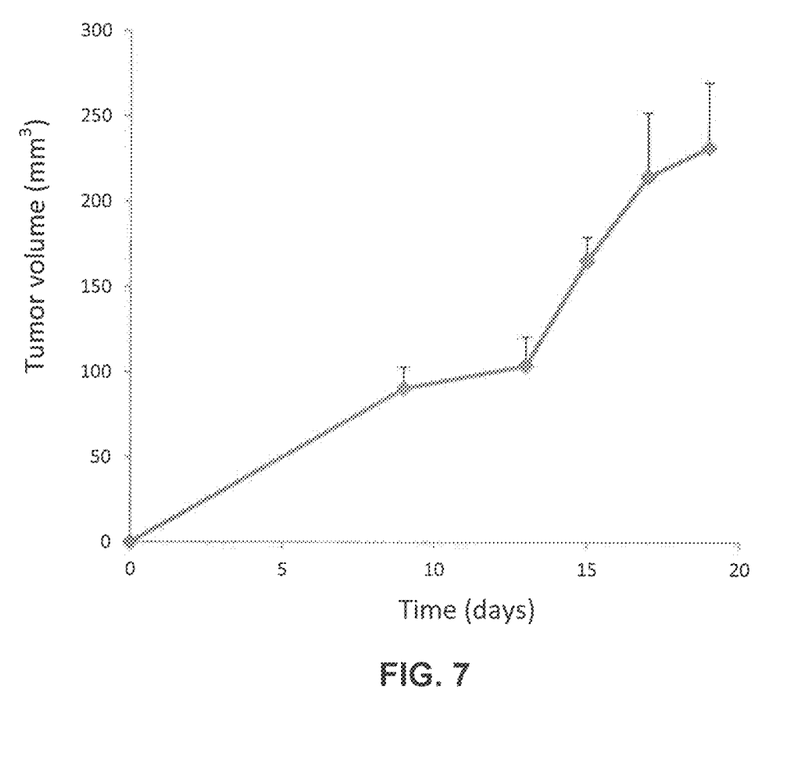
FIG. 7 presents the tumor growth rate of MCF7 ER(+) breast cancer cells admixed with human HFFF2 fibroblasts showing average tumor volume.

It was hypothesized that stromal fibroblasts may increase the tumorigenicity of MCF7 cells and an additional experiment was performed in which increased numbers of HFFF2 fibroblasts were admixed with the MCF7 cells prior to cell inoculation (3 million HFFF2 and 3 million MCF7). Consistent with this hypotheses, in this experiment 4 out of 5 animals had tumors that grew to an average volume of about 250 $mm^3$ (FIG. 6, FIG. 7).

This study demonstrates the feasibility of using *P. californicus* for the growth of ER positive breast cancers in vivo without exogenous E2 supplementation. The fact that E2 levels in *P. californicus* approximate those of postmenopausal women who develop about half of the ER-positive breast cancers offers a model that may be particularly pertinent for the study of this cohort of breast cancer patients. Collectively, through appropriate genetic manipulation or optimization of CsA-mediated immunosuppression *P. californicus* may provide an attractive alternative to mice in modeling ER(+) breast cancers in vivo.

While certain embodiments of the disclosed subject matter have been described using specific terms, such description is for illustrative purposes only, and it is to be understood that changes and variations may be made without departing from the spirit or scope of the subject matter.

What is claimed is:

1. An immunosuppressed *Peromyscus californicus* mouse comprising, an estrogen receptor negative ER (−) or estrogen receptor positive ER (+) xenograft human breast cancer cells admixed with human stromal fibroblasts, wherein the xenograft ER (−) or ER (+) breast cancer cells admixed with human stromal fibroblasts have been implanted in the *Peromyscus californicus* mouse, and wherein the mouse exhibits ER (−) or ER (+) breast tumor growth as a result of the xenograft implantation.

2. The mouse of claim 1, wherein the mouse is an outbred mouse.

3. The mouse of claim 1, wherein the xenograft cancer cells comprise biopsy cells or ex vivo cancer cells.

4. The mouse of claim 1, further comprising a detectable label associated with the xenograft cancer cells.

* * * * *